US012042323B2

(12) United States Patent
Tao

(10) Patent No.: US 12,042,323 B2
(45) Date of Patent: Jul. 23, 2024

(54) SYSTEMS AND METHODS FOR DIGITAL RADIOGRAPHY

(71) Applicant: SHANGHAI UNITED IMAGING HEALTHCARE CO., LTD., Shanghai (CN)

(72) Inventor: Xunsan Tao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 18/168,536

(22) Filed: Feb. 13, 2023

(65) Prior Publication Data

US 2023/0190217 A1 Jun. 22, 2023

Related U.S. Application Data

(60) Division of application No. 17/445,613, filed on Aug. 23, 2021, now Pat. No. 11,576,642, which is a
(Continued)

(30) Foreign Application Priority Data

Sep. 20, 2017 (CN) .......................... 201710850958.3

(51) Int. Cl.
*A61B 6/00* (2024.01)
*A61B 6/42* (2024.01)

(52) U.S. Cl.
CPC .............. *A61B 6/54* (2013.01); *A61B 6/4208* (2013.01); *A61B 6/4266* (2013.01); *A61B 6/44* (2013.01);
(Continued)

(58) Field of Classification Search
CPC ....... A61B 6/54; A61B 6/4266; A61B 6/4452; A61B 6/5205; A61B 6/563; A61B 6/542;
(Continued)

(56) References Cited

U.S. PATENT DOCUMENTS 7,386,157 B2 6/2008 Tago et al.
7,429,737 B2 9/2008 Wojcik et al.
(Continued)

FOREIGN PATENT DOCUMENTS

CN 2705120 Y 6/2005
CN 203852366 U 10/2014
(Continued)

OTHER PUBLICATIONS

International Search Report in PCT/CN2018/105702 mailed on Nov. 29, 2018, 5 pages.
(Continued)

*Primary Examiner* — Don K Wong
(74) *Attorney, Agent, or Firm* — METIS IP LLC

(57) ABSTRACT

Systems and methods for digital radiography are provided. The method may be implemented on the implemented on a DR system including an imaging device and a computing device. The computing device may include at least one processor and at least one storage device. The method may include directing multiple dose sensors to detect a dose of radiation rays emitted from a radiation source of the imaging device. The multiple dose sensors may correspond to multiple imaging detectors, respectively. The method may also include determining the dose of the radiation rays. The method may further include directing, based on the dose of the radiation rays, at least one imaging detector of the multiple imaging detectors to proceed to detect the radiation rays for generating an image of a target object to be examined.

20 Claims, 10 Drawing Sheets

Related U.S. Application Data division of application No. 16/236,588, filed on Dec. 30, 2018, now Pat. No. 11,096,647, which is a continuation of application No. PCT/CN2018/105702, filed on Sep. 14, 2018.

(52) U.S. Cl.
CPC .......... *A61B 6/4452* (2013.01); *A61B 6/5205* (2013.01); *A61B 6/563* (2013.01)

(58) Field of Classification Search
CPC ....... A61B 6/547; A61B 6/566; A61B 6/4275; A61B 6/44; A61B 6/06; A61B 6/488; A61B 6/486; A61B 6/5211; A61B 6/5294; G06T 7/0016; G06T 11/60; G06T 2207/10116; G06T 1/171; G06T 1/20; G06T 7/005; G06T 7/0097; G06T 2207/20221; G06T 2207/30061; G06T 7/0014; G06T 7/30; G06K 9/6212; G01N 2021/1765
See application file for complete search history.

(56) References Cited

U.S. PATENT DOCUMENTS

| | | | |
|---|---|---|---|
| 8,821,015 | B2 | 9/2014 | Stagnitto et al. |
| 2009/0060136 | A1 | 3/2009 | Tamakoshi |
| 2011/0249791 | A1* | 10/2011 | Wang .................... A61B 6/547 378/62 |
| 2013/0136234 | A1 | 5/2013 | Noma et al. |
| 2013/0182823 | A1 | 7/2013 | Kuwabara |
| 2013/0307923 | A1 | 11/2013 | Inglese et al. |
| 2015/0110245 | A1 | 4/2015 | Kim et al. |
| 2015/0192684 | A1 | 7/2015 | Ito |
| 2016/0015340 | A1 | 1/2016 | Nenoki et al. |
| 2018/0018772 | A1 | 1/2018 | Fujiwara et al. |
| 2019/0175135 | A1 | 6/2019 | Tao |

FOREIGN PATENT DOCUMENTS

| | | | |
|---|---|---|---|
| CN | 104856710 | A | 8/2015 |
| CN | 204683628 | U | 10/2015 |
| CN | 205514635 | U | 8/2016 |
| CN | 105989092 | A | 10/2016 |
| CN | 106846318 | A | 6/2017 |
| EP | 2944257 | A1 | 11/2015 |
| EP | 3050510 | A1 | 8/2016 |
| JP | 2007252760 | A | 10/2007 |
| JP | 2016135176 | A | 7/2016 |
| RU | 2597026 | C1 | 9/2016 |

OTHER PUBLICATIONS

Written Opinion in PCT/CN2018/105702 mailed on Nov. 29, 2018, 6 pages.
The Extended European Search Report in European Application No. 18859384.2 mailed on Feb. 11, 2021, 8 pages.
The Second Office Action in Chinese Application No. 201710850958.3 mailed on Nov. 1, 2019, 26 pages.
First Office Action in Russian Application No. 2020114050 mailed on Nov. 11, 2020, 23 pages.
Notice of Preliminary Rejection in Korean Application No. 10-2020-7011432 mailed on Oct. 12, 2021, 20 pages.
First Examination Report in Australian Application No. 2021290363 mailed on Oct. 20, 2022, 4 pages.

* cited by examiner

SYSTEMS AND METHODS FOR DIGITAL RADIOGRAPHY

CROSS-REFERENCE TO RELATED APPLICATIONS

This application is a divisional application of U.S. application Ser. No. 17/445,613, filed on Aug. 23, 2021, which is a divisional application of U.S. application Ser. No. 16/236,588 (now U.S. Pat. No. 11,096,647), filed on Dec. 30, 2018, which is a continuation of International Application No. PCT/CN2018/105702, filed on Sep. 14, 2018, which claims priority of Chinese Patent Application No. 201710850958.3, filed on Sep. 20, 2017, the entire contents of which are hereby incorporated by reference.

TECHNICAL FIELD

The present disclosure generally relates to medical devices, and in specifically, to systems and methods for imaging using a Digital Radiography (DR) system.

BACKGROUND

X-ray imaging is a technology that uses an X-ray scanner to scan an object to generate an image of the object. The X-ray imaging technology, such as a Digital Radiography (DR) system, has been widely used in medical diagnosis, radiation therapy planning, surgery planning, and other medical procedures. In the DR system, X-ray detectors are important components for photography and/or imaging of a target object (e.g., a body part of a patient). In some scenarios, the current DR system may need to select a particular X-ray detector from multiple X-ray detectors corresponding to different positions of a patient for imaging by recognizing physical labels set on the detectors, which may increase manufacturing costs of the DR system and compromise the imaging efficiency. Thus, it is desirable to provide an efficient system and method for imaging using the DR system.

SUMMARY

In one aspect of the present disclosure, a method implemented on a DR system is provided. The DR system may include an imaging device and a computing device. The computing device may include at least one processor and at least one storage device. The method may include directing a dose sensor to detect a dose of radiation rays emitted from a radiation source of the imaging device, wherein the multiple dose sensors correspond to multiple imaging detectors, respectively; determining the dose of the radiation rays; and directing, based on the dose of the radiation rays, at least one of the multiple imaging detectors corresponding to the multiple dose sensors to proceed to detect the radiation rays for generating an image of a target object to be examined.

According to some embodiments of the present disclosure, the radiation rays may include X-rays.

According to some embodiments of the present disclosure, the method may further include determining whether more than one of the least one of the multiple imaging detectors is needed to detect the radiation rays; and in response to the determination that there is only one of the least one imaging detector needed to detect the radiation rays, obtaining a signal from the only one of the least one imaging detector; and generating the image of the target object based on the obtained signal.

According to some embodiments of the present disclosure, the method may further include in response to the determination that there is more than one of the least one imaging detector needed to detect the radiation rays, obtaining radiation data from the more than one of the at least one imaging detector; obtaining reference data associated with the target object; and generating the image of the target object based on the radiation data that is the closest to the reference data.

According to some embodiments of the present disclosure, directing the at least one imaging detector to obtain radiation rays may include determining whether the dose of the radiation rays obtained from one of the multiple dose sensors is larger than or equal to a preset dose; and in response to the determination that the dose of the radiation rays obtained by the one of the multiple dose sensors is larger than or equal to the preset dose, directing one of the multiple imaging detectors corresponding to the one of the multiple dose sensors obtaining the dose larger than or equal to the preset dose to proceed to detect the radiation rays.

According to some embodiments of the present disclosure, the method may further include in response to the determination that dose of the radiation rays obtained from two or more of the multiple dose sensors is larger than or equal to the preset dose, directing one of the multiple imaging detectors to proceed to detect the radiation rays, wherein the one of the multiple imaging detectors corresponds to a dose sensor of the multiple dose sensors that detects a largest dose of the radiation rays.

According to some embodiments of the present disclosure, when the at least one of multiple imaging detectors proceeds to detecting the radiation rays, the multiple dose sensors may stop detecting the radiation rays.

According to some embodiments of the present disclosure, a dose sensor of the multiple dose sensors and an imaging detector of the multiple imaging detectors corresponding to the dose sensor are integrated into a radiation detector.

According to some embodiments of the present disclosure, the method may further comprise: obtaining a request for generating the image of the target object; and directing the radiation source to produce the radiation rays in response to the request for generating the image of the target object.

In another aspect of the present disclosure, a method implemented on a DR system is provided. Th DR system may include a radiation source, multiple imaging detectors, and a computing device. The computing device may include at least one processor and at least one storage device. The method may include obtaining a request for generating an image of a target object; directing the radiation source to produce radiation rays in response to the request; and directing, based on at least a portion of the radiation rays received by the at least one imaging detector, one of the multiple imaging detectors to detect the radiation rays for generating the image of the target object.

In another aspect of the present disclosure, a method implemented on a DR system is provided. Th DR system may include a radiation source, multiple imaging detectors, and a computing device. The computing device may include at least one processor and at least one storage device. The method may include obtaining a request for generating an image of a target object; directing a radiation source of the imaging device to produce radiation rays in response to the request for generating the image of the target object; obtaining radiation data from multiple detectors of the imaging device; obtaining reference data associated with the target object; and generating the image of the target object based on the radiation data and the reference data.

According to some embodiments of the present disclosure, the generating the image of the target object based on the radiation data and the reference data may include determining a similarity value, to the reference data, of the radiation data obtained from the multiple detectors, wherein each of the similarity value corresponds to the radiation data obtained from one of the multiple detectors; determining a highest similarity value, to the reference data, of the radiation data obtained from the multiple detectors; and generating the image of the target object based on the radiation data corresponding to the highest similarity value.

In another aspect of the present disclosure, a method implemented on a DR system is provided. Th DR system may include a radiation source, multiple imaging detectors, and a computing device. The computing device may include at least one processor and at least one storage device. The method may include obtaining a request for generating an image of a target object; directing the radiation source to produce radiation rays in response to the request; directing, based on at least a portion of the radiation rays received by the multiple imaging detectors, at least one of the multiple imaging detectors to detect the radiation rays for generating the image of the target object; and determining whether the number of the at least one of the multiple imaging detectors is more than one, in response to the determination that the number of the imaging detectors is one, designating an image generated by the one imaging detector as the image of the target object; and in response to the determination that the number of the imaging detectors is more than one, designating an image that is closest to a reference image as the image of the target object.

In another aspect of the present disclosure, a digital X-ray radiography system is provided. The digital X-ray radiography system may include a controller, an X-ray source and two flat-plate shaped imaging detectors. The two flat-plate shaped radiation detectors may be respectively arranged on a first orientation and a second orientation. An angle between the first orientation and the second orientation may be between 60 degrees and 120 degrees. The X-ray source may be disposed opposite to the two flat-plate shaped imaging detectors. The X-ray source's relative position between the two detectors may be adjustable. The controller may be configured to receive an image acquisition instruction, to control the X-ray source to provide X-rays according to the image acquisition instruction, and to initiate one of the two flat-plate shaped imaging detectors to acquire X-rays for generating an image of a target object to be examined based on at least a portion of the X-rays received by the two flat-plate shaped imaging detectors, or to generate the image of the target object based on the X-rays acquired in the one of the two flat-plate shaped imaging detectors.

In another aspect of the present disclosure, a DR system including an imaging device is provided. The system may include at least one storage device storing a set of instructions, and at least one processor in communication with the at least one storage medium. When executing the set of instructions, the at least one processor may be configured to cause the system to direct multiple dose sensors to detect a dose of radiation rays emitted from a radiation source of the imaging device, wherein the multiple dose sensors correspond to multiple imaging detectors, respectively; determine the dose of the radiation rays; and direct, based on the dose of the radiation rays, at least one of the multiple imaging detectors corresponding to the multiple dose sensors to proceed to detect the radiation rays for generating an image of a target object to be examined.

In another aspect of the present disclosure, a non-transitory computer readable medium including at least one set of instructions may be provided. When executed by at least one processor of a computing device, the at least one set of instructions may cause the at least one processor to effectuate a method. The method may include directing multiple dose sensors to detect a dose of radiation rays emitted from a radiation source of the imaging device, wherein the multiple dose sensors correspond to multiple imaging detectors; determining the dose of the radiation rays; and directing, based on the dose of the radiation rays, at least one of the multiple imaging detectors corresponding to the multiple dose sensors to proceed to detect the radiation rays for generating an image of a target object to be examined.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
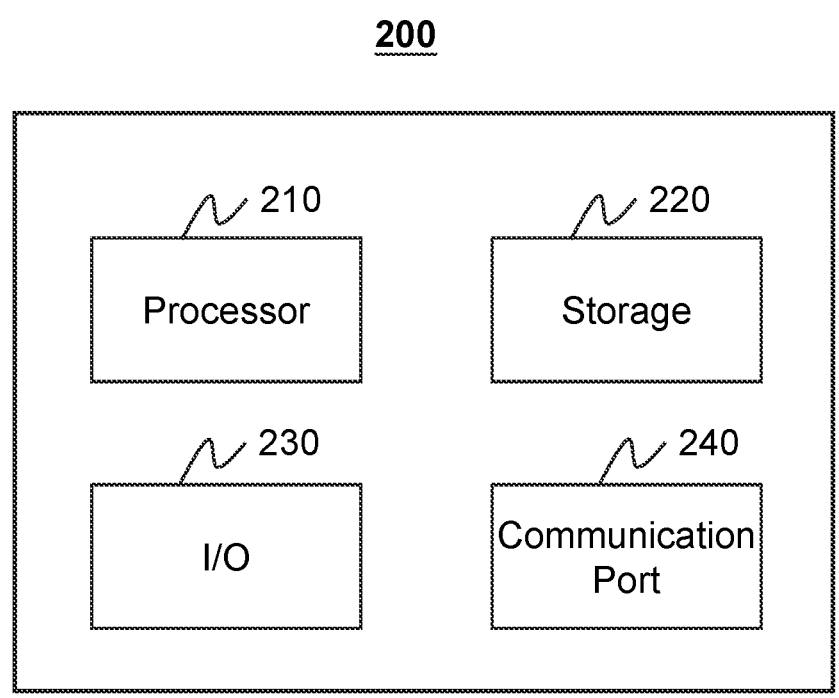
FIG. 2 is a schematic diagram illustrating exemplary hardware and/or software components of a computing device 200 on which the processing device 120 may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure relates to systems and methods for detecting radiation rays for imaging in a DR system. The DR system may include an imaging device including an X-ray source and multiple radiation detectors. In some embodiments, the DR system in the present disclosure may direct at least one of the multiple radiation detectors to obtain radiation rays emitted from the X-ray source based on radiation doses received by the multiple radiation detectors, and generate an image of a target object based on the obtained radiation rays. If only one radiation detector is directed to receive radiation rays, the DR system may designate the image generated based on radiation rays received by the radiation detector as the image of the target object. If more than one radiation detectors are directed to receive radiation rays, the DR system may designate, based on reference data associated with the target object, an image from images generated based on radiation rays received by the more than one radiation detectors as the image of the target object.

It should be noted that the imaging system 100 described below is merely provided for illustration purposes, and not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Provided herein are systems and components for non-invasive imaging, such as for disease diagnosis or research purposes. In some embodiments, the imaging system may be a digital radiography (DR) system, computed tomography (CT) system, a positron emission tomography (PET) system, an emission computed tomography (ECT) system, a magnetic resonance imaging (MRI) system, an ultrasonography system, an X-ray photography system, or the like, or any combination thereof.

Figure 1:
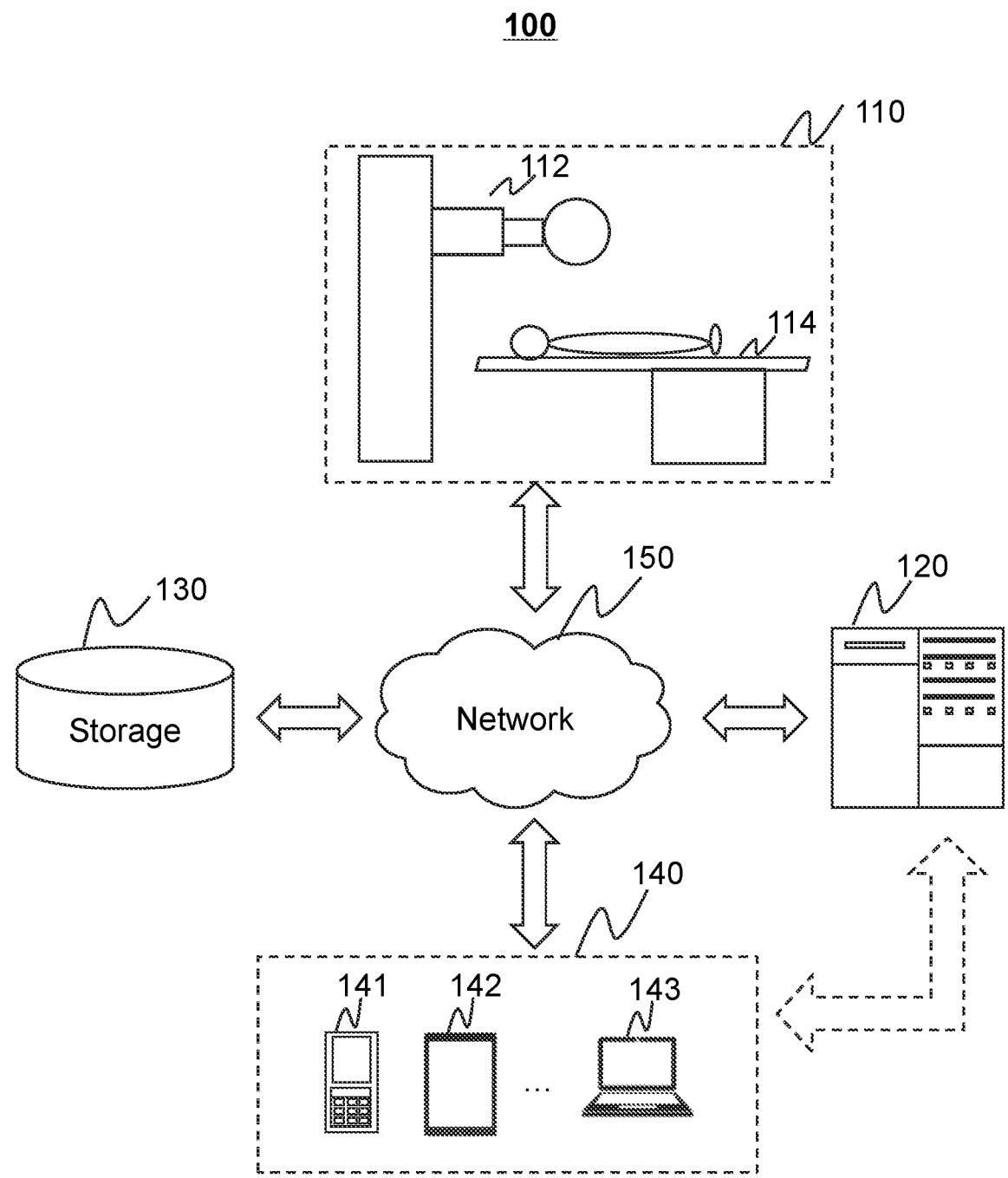
FIG. 1 is a schematic diagram illustrating an exemplary imaging system 100 according to some embodiments of the present disclosure.

FIG. 1 is a schematic diagram illustrating an exemplary imaging system 100 according to some embodiments of the present disclosure. Merely for illustration purposes, the imaging system 100 may be a DR system. As shown in FIG. 1, the imaging system 100 (also referred to as a DR system 100) may include an X-ray imaging device 110, a processing device 120, a storage device 130, one or more terminal(s) 140, and a network 150. In some embodiments, the X-ray imaging device 110, the processing device 120, the storage device 130, and/or the terminal(s) 140 may be connected to and/or communicate with each other via a wireless connection (e.g., the network 150), a wired connection, or a combination thereof. The connections between the components in the imaging system 100 may vary. Merely by way of example, the X-ray imaging device 110 may be connected to the processing device 120 through the network 150, as illustrated in FIG. 1. As another example, the X-ray imaging device 110 may be connected to the processing device 120 directly. As a further example, the storage device 130 may be connected to the processing device 120 through the network 150, as illustrated in FIG. 1, or connected to the processing device 120 directly. As still a further example, the terminal(s) 140 may be connected to the processing device 120 through the network 150, as illustrated in FIG. 1, or connected to the processing device 120 directly.

The X-ray imaging device 110 may include a gantry 112, a detector, and a table 114. The gantry 112 may include a body, a gantry head, a transmission assembly, etc. The body may be configured to support a component of the X-ray imaging device 110, such as the gantry head. The gantry head may be equipped with an X-ray source configured to generate and/or emit X-rays. The transmission assembly may be configured to move the gantry head. The table 114 may be configured to support a subject (e.g., a patient) to be examined. The detector may be configured to detect X-rays passing through a subject for dose determination and/or imaging. In the present disclosure, "subject" and "object" are used interchangeably. Details of the X-ray scanner 100 of the DR system 100 may be found elsewhere in the present disclosure, e.g., in FIG. 4 or 10 and the descriptions thereof.

The processing device 120 may process data and/or information obtained from the X-ray imaging device 110, the storage device 130, and/or the terminal(s) 140. For example, the processing device 120 may generate an image relating to at least one part of a subject (e.g., a tumor of a patient) based on image data collected by the X-ray imaging device 110. As another example, the processing device 120 may determine a specific position of the gantry head of the X-ray imaging device 110. Then, the processing device 120 may control the transmission assembly of the X-ray imaging device 110 to move the gantry head to the specific position. In some embodiments, the processing device 120 may be a single server or a server group. The server group may be centralized or distributed. In some embodiments, the processing device 120 may be local or remote. For example, the processing device 120 may access information and/or data from the X-ray imaging device 110, the storage device 130, and/or the terminal(s) 140 via the network 150. As another example, the processing device 120 may be directly connected to the X-ray imaging device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof.

The storage device 130 may store data, instructions, and/or any other information. In some embodiments, the storage device 130 may store data obtained from the X-ray imaging device 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the imaging system 100 (e.g., the processing device 120, the terminal(s) 140). One or more components in the imaging system 100 may access the data or instructions stored in the storage device 130 via the network 150. In some embodiments, the storage device 130 may be part of the processing device 120.

The terminal(s) 140 may be connected to and/or communicate with the X-ray imaging device 110, the processing device 120, and/or the storage device 130. For example, the terminal(s) 140 may obtain a processed image from the processing device 120. As another example, the terminal(s) 140 may obtain image data acquired via the X-ray imaging device 110 and transmit the image data to the processing device 120 to be processed. In some embodiments, the terminal(s) 140 may include a mobile device 141, a tablet computer 142, a laptop computer 143, or the like, or any combination thereof. For example, the mobile device 140-1 may include a mobile phone, a personal digital assistant (PDA), a gaming device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate the exchange of information and/or data for the imaging system 100. In some embodiments, one or more components of the imaging system 100 (e.g., the X-ray imaging device 110, the processing device 120, the storage device 130, the terminal(s) 140, etc.) may communicate information and/or data with one or more other components of the imaging system 100 via the network 150. For example, the processing device 120 may obtain image data from the X-ray imaging device 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 130 may be a data storage including cloud computing platforms, such as public cloud, private cloud, community, and hybrid clouds, etc. However, those variations and modifications do not depart the scope of the present disclosure.

FIG. 2 is a schematic diagram illustrating exemplary hardware and/or software components of a computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process radiation dose data and/or image data obtained from the imaging device 110, the terminal(s) 140, the storage device 130, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus, operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the imaging device 110, the terminal(s) 140, the storage device 130, and/or any other component of the imaging system 100. In some embodiments, the storage 220 may include a mass storage, removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for determining one or more registration parameters related to multi-modality images acquired by the imaging system 100.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 150) to facilitate data communications. The communication port 240 may establish connections between the processing device 120 and the imaging device 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or any combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
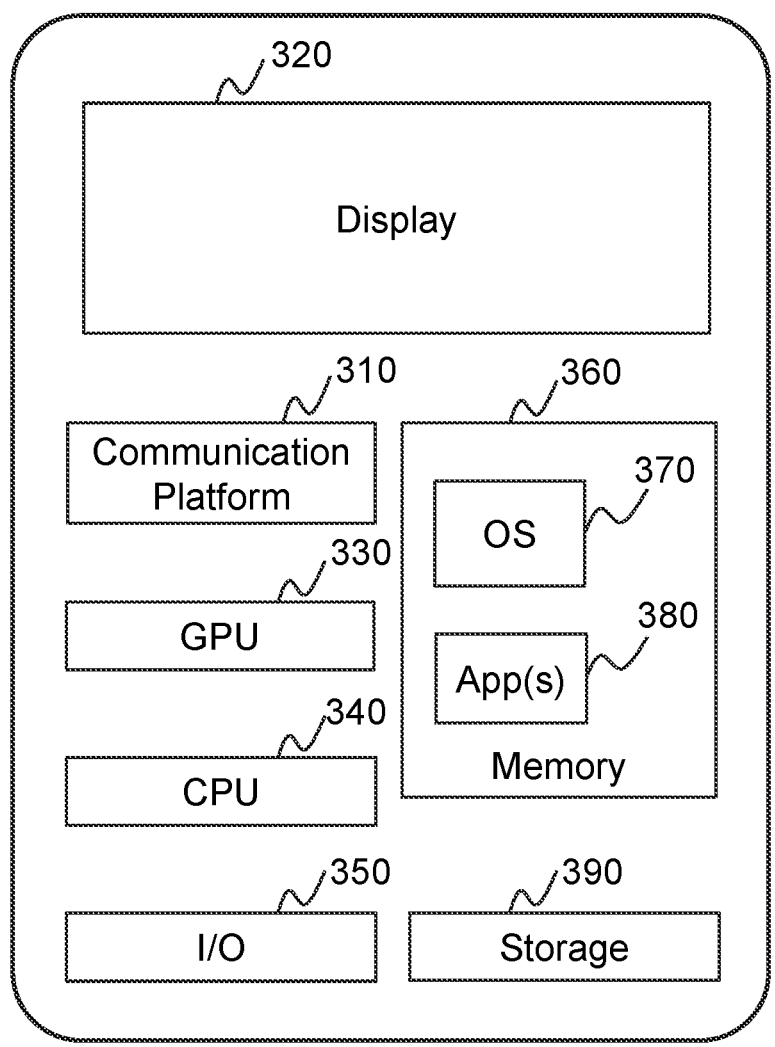
FIG. 3 is a schematic diagram illustrating exemplary hardware and/or software components of a mobile device 300 on which the terminal(s) 140 may be implemented according to some embodiments of the present disclosure.

FIG. 3 is a schematic diagram illustrating exemplary hardware and/or software components of a mobile device 300 on which the terminal(s) 140 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information respect to image processing or other information from the processing device 120. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of workstation or external device. A computer may also act as a server if appropriately programmed.

Figure 4:
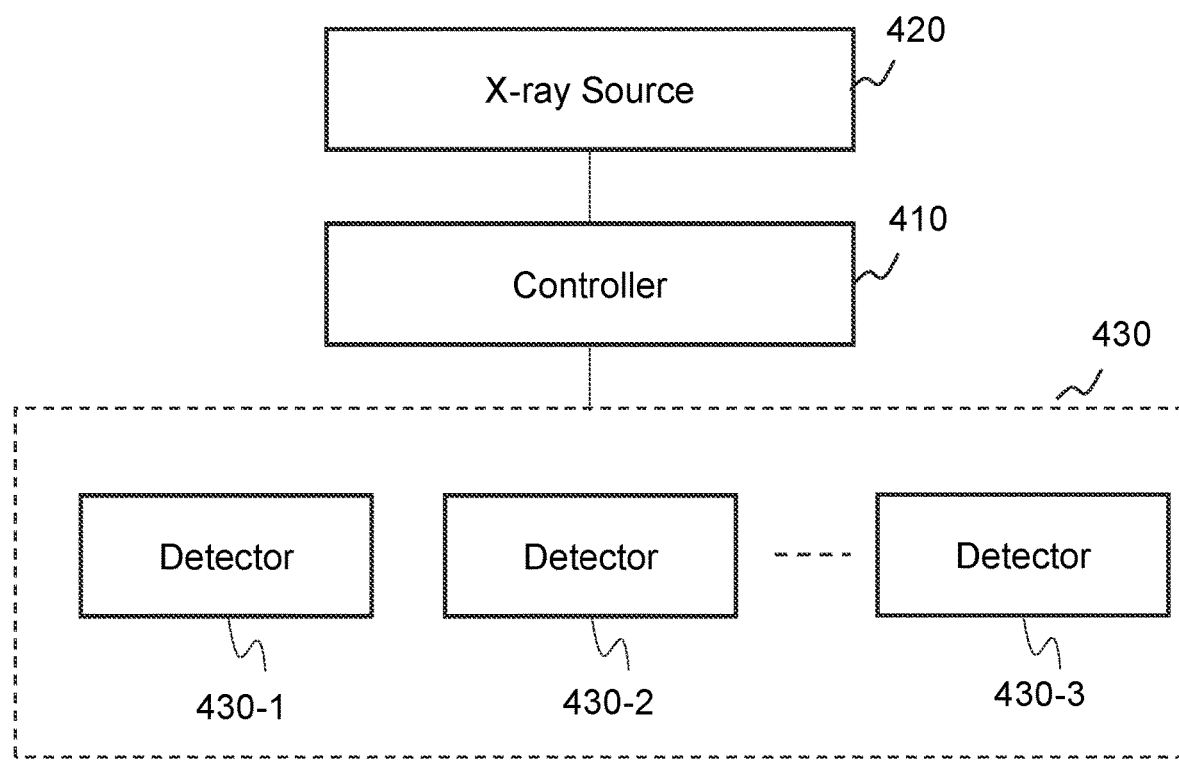
FIG. 4 is a schematic diagram illustrating an exemplary DR system according to some embodiments of the present disclosure.

FIG. 4 is a schematic diagram illustrating an exemplary DR system according to some embodiments of the present disclosure. As illustrated in FIG. 4, the DR system 100 may include an X-ray source 420, a controller 410, and at least two detectors 430. The controller 410 may be configured to control the X-ray source 420 to generate or emit X-rays, and/or control the at least two detectors 430 to detect X-rays for imaging. The controller 410 may connect with the X-ray source 420, and the at least two detectors 430 separately. In some embodiments, the controller 410 may perform same operations that the processing device 120 (as shown in FIG. 1) performs.

The at least two detectors 430 may include flat panel detectors. The at least two detectors 430 may be set at different positions with respect to the X-ray source 420 to detect X-rays from different orientations. For example, when a patient lies on the table 114, the DR system 100 may use a detector set in a flat-bed film magazine parallel to the table 114 to detect X-rays emitted from the X-ray source 420. As another example, when the patient stands in front of the imaging device (not shown in the figure) of the DR system 100 (e.g., to exam the lung of the patient), the DR system 100 may use a detector set in a chest film magazine near the chest of the patient to detect X-rays emitted from the X-ray source 420.

In some embodiments, a detector of the at least two detectors 430 may include a dose sensor and an imaging detector (not shown in the figure). The dose sensor may be configured to detect a dose of X-rays emitted from the X-ray source 420. The imaging detector may be configured to receive X-rays emitted from the X-ray source 420, and generate an image based on the received X-rays. In some embodiments, the dose sensor and the imaging detector may be encapsulated in a housing of the detector. In some embodiments, the dose sensor and the imaging detector may operate simultaneously or in a particular order. For example, the imaging detector may start to detect X-rays after the controller 410 determines a dose of X-rays obtained by the dose sensor.

In some embodiments, a first detector (e.g., a detector 430-1) of the at least two detectors 430 may include or be an imaging detector for receiving X-rays for imaging. The imaging detector may correspond to a dose sensor for dose detection. The dose sensor may be encapsulated in a second detector (e.g., the detector 430-2), and may be associated with the imaging detector of the first detector. For example, the controller 410 may determine a dose of X-rays detected by a dose sensor in a detector 430-2, and direct the imaging detector in the detector 430-1 to proceed to detect the radiation rays for generating an image of a target object to be examined.

In some embodiments, the DR system 100 may further include an output device (e.g., the I/O 230, or the I/O 350). The output device may be configured to output images generated based on image data received from the detector 430. In some embodiments, the output device may be a display device for displaying the output images.

Figure 5:
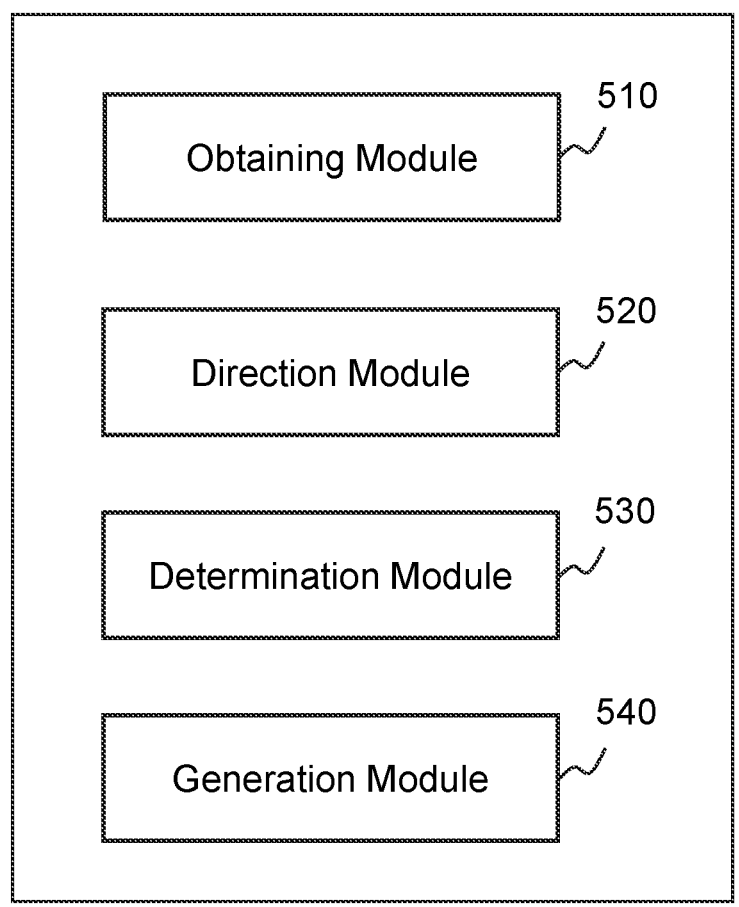
FIG. 5 is a block diagram illustrating exemplary processing device according to some embodiments of the present disclosure.

FIG. 5 is a block diagram illustrating exemplary processing device according to some embodiments of the present disclosure. The processing device 120 (or the controller 410) may be implemented on the computing device 200 (e.g., the processor 210) illustrated in FIG. 2. Merely by way of example, the processing device 120 (or the controller 410) may include an obtaining module 510, a direction module 520, a determination module 530, and a generation module 540.

The obtaining module 510 may be configured to acquire data for generating an image of a target object. In some embodiments, the obtaining module 510 may receive a request for generating the image of the target object. The request may be sent by a user or the DR system 100 automatically. In some embodiments, the obtaining module 510 may obtain radiation rays detected from at least one detector (e.g., at least one imaging detector). The obtaining module 510 may store the detected radiation rays in forms of radiation data. In some embodiments, the obtaining module 510 may obtain reference data associated with the target object. The reference data may be pre-stored in the DR system 100 or stored in an independent database.

The direction module 520 may be configured to control one or more components of the DR system 100. In some embodiments, the direction module 520 may direct a radiation source to generate or emit radiation rays after the obtaining module 510 receives the request for generating the image of the target object. In some embodiments, the direction module 520 may direct one or more detectors of the DR system to proceed to detect radiation rays. For example, the direction module 520 may direct one or more dose sensors of the DR system 100 for detecting doses of radiation rays emitted from the radiation source. As another example, the direction module 520 may direct one or more imaging detectors of the DR system 100 to detect radiation rays for generating the image of the target object. As another example, the direction module 520 may direct the one or more dose sensors to stop detecting radiation rays immediately after the direction module 520 directs the imaging detector(s) to obtain radiation rays emitted from the radiation source for generating an image.

The determination module 530 may be configured to determine whether a condition is met for generating the image of the target object. In some embodiments, the determination module 530 may determine doses of the radiation rays detected by the one or more dose sensors. The determination module 530 may determine whether the dose detected by the one or more dose sensors is larger or equal to a threshold (also referred to as a "preset dose"). In some embodiments, the determination module 530 may determine whether the number of the one or more imaging detectors is more than one. In some embodiments, the determination module 530 may designate an image that has the highest similarity value with the reference data as the image of the target object.

The generation module 540 may be configured to generate an image based on the radiation rays detected by the one or more imaging detectors. In some embodiments, the generation module 540 may obtain a signal from one of the one or more imaging detectors. The obtained signal may be a digital signal including information of the detected radiation rays (e.g., attenuation information of X-rays). The generation module 540 may generate an image based on the obtained signal.

In some embodiments, the obtaining module 510, the direction module 520, the determination module 530 and the generation module 540 may communicate with each other by a communication module (not shown in FIG. 5). For example, the communication module may receive information of the dose determination from the determination module 530 and send the dose determination to the direction module 520 for directing the one or more imaging detectors.

It should be noted that the above description of the processing device 120 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, any module mentioned above may be implemented in two or more separate units. For example, the functions of direction module 520 may be implemented in two separate units, one of which is configured to direct a dose sensor to detect a dose of radiation rays, and the other is configured to direct an imaging detector to detect the radiation rays for imaging. In some embodiments, one or more of the modules may be implemented as one unit. Merely by way of example, the direction module 520 and the determination module 530 may be integrated as one module.

Figure 6:
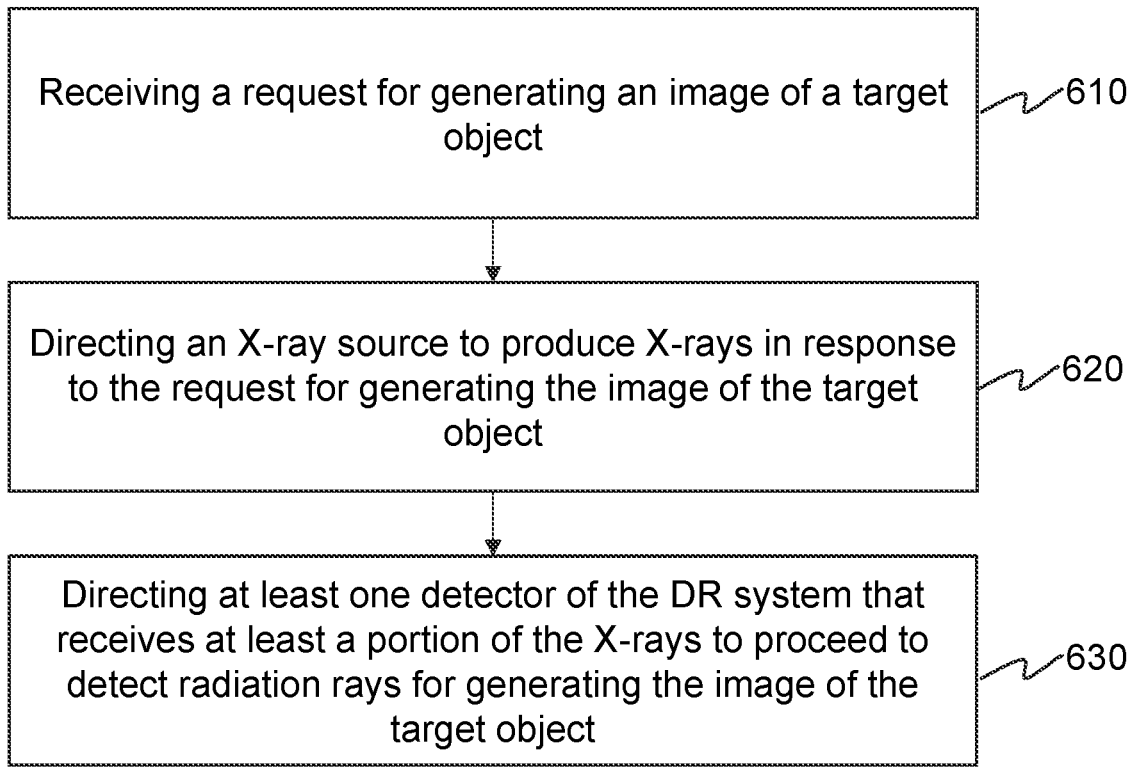
FIG. 6 is a flowchart illustrating an exemplary process for directing at least one detector of the DR system 100 to detect radiation rays (e.g., X-rays) for generating an image of a target object to be examined according to some embodiments of the present disclosure.

FIG. 6 is a flowchart illustrating an exemplary process for directing at least one detector of the DR system 100 to detect radiation rays (e.g., X-rays) for generating an image of a target object to be examined according to some embodiments of the present disclosure. In some embodiments, one or more operations of process 600 illustrated in FIG. 6 for imaging may be implemented in the DR system 100 illustrated in FIG. 1. For example, the process 600 illustrated in FIG. 6 may be stored in the storage device 130 in the form of instructions, and invoked and/or executed by the processing device 120 (e.g., the processor 210 of the computing device 200 as illustrated in FIG. 2, the CPU 340 of the mobile device 300 as illustrated in FIG. 3). As another example, a portion of the process 600 may be implemented on the X-ray imaging device 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 6 and described below is not intended to be limiting.

In 610, the processing device 120 (e.g., the obtaining module 510) may receive a request for generating an image of a target object. Exemplary target object may include a patient to be examined. In some embodiments, the request may be sent by a user (e.g., a technician, a doctor, etc.), or sent by the DR system 100 automatically. For example, a user may determine a region of interest (e.g., a tissue of the patient) to be examined based on information of the target object. The user may send the request after the gantry 112 of the DR system 100 is moved to a designated position based on the region of interest. As another example, the DR system 100 may obtain an information card of the target object when the target object enters an examination room. The information card may include identity information of the target object and the region of interest to be examined. The DR system 100 may read the information card, and direct the gantry 112 to move to a designated position based on the region of interest in the information card. Then the DR system 100 may send instruction to the radiation source 112 for generating or emitting X-rays after the gantry 112 is moved to the designated position.

In 620, the processing device 120 (e.g., the direction module 520) may direct an X-ray source to produce X-rays in response to the request for generating the image of the target object. The direction module 520 may direct the X-ray source to generate or emit X-rays after the obtaining module 510 receives the request. In some embodiments, the direction in which X-rays are emitted may be fixed after the position of the DR system 100 (e.g., the position of the gantry 112) is determined.

In 630, the processing device 120 (e.g., the direction module 520) may direct at least one detector of the DR system 100 that receives at least a portion of the X-rays to proceed to detect radiation rays (e.g., X-rays) for generating the image of the target object.

In some embodiments, the determination module 530 may determine at least a portion of the X-rays (also referred to as radiation rays) received by the at least one detector. The at least one detector may be or include at least one imaging detector. In some embodiments, an imaging detector may be integrated with or communicate with a detector (e.g., a dose detector or a dose sensor) that can detect the portion of the X-rays once the imaging detector receives the portion of the X-rays. In some embodiments, the direction module 520 may direct one of the at least one detector to detect X-rays for generating the image of the target object, for example, the one of the at least one detector is a detector that receives the highest dose of X-rays.

In some embodiments, the direction module 520 may direct one or more detectors of the at least one detector to detect X-rays for generating the image of the target object, for example, each of the one or more detectors receive a dose of X-rays that is greater than or equal to a predetermined value. The determination module 530 may further determine whether the number of the one or more detectors is more than one. In response to the determination that the number of one or more detectors is one, an image generated by the one detector may be designated as the image of the target object. In response to the determination that the number of the one or more detectors is more than one, the more than one detector may generate more than one image. The imaging system 100 may designate one from the more than one image as the image of the target object. The designated image may be closer to a reference image associated with the target object than other images of the more than one image.

In some embodiments, the DR system 100 may include multiple detectors. Each of the multiple detectors may include a dose sensor and an imaging detector, i.e. multiple dose sensors included in the multiple detectors respectively correspond to multiple imaging detectors included in the multiple detectors. The direction module 520 may direct multiple dose sensors of the multiple detectors to detect doses of radiation rays emitted from the radiation source of the imaging device 110 actively. The determination module 530 may determine the doses of the radiation rays detected by the multiple dose sensors. Then the direction module 520 may direct, based on doses of radiation rays (e.g., X-rays) detected by the multiple dose sensors of the DR system 100, at least one of multiple imaging detectors corresponding to the multiple dose sensors to proceed to detect the radiation rays for generating an image of a target object to be examined. For example, when the DR system 100 scans the target object, the multiple dose sensors may detect doses of radiation rays (e.g., X-rays) emitted from the X-ray source. The direction module 520 may select at least one target detector from the multiple detectors based on the doses of radiation rays (e.g., X-rays) detected by the multiple dose sensors. The direction module 520 may direct at least one imaging detector included in the at least one target detector to obtain radiation rays (e.g., X-rays) for generating the image of the target object.

In some embodiments, the system 100 may include multiple detectors. A first number of detectors of the multiple detectors may only include dose sensors, and a second number of detectors of the multiple detectors may only include imaging detectors. A detector including a dose sensor may correspond to and/or communicate with another detector including an imaging detector. The direction module 520 may direct, for example, by executing program codes generated by the imaging system 100 based on doses of radiation rays (e.g., X-rays) detected by the first number of detectors including the dose sensors, at least one of the second number of detectors including the imaging detectors to proceed to detect the radiation rays for generating an image of a target object to be examined. In some embodiments, the first number may be equal to the second number.

In some embodiments, the processing device 120 (e.g., the determination module 530) may determine whether the dose detected by a detector is larger or equal to a threshold (also referred to as a "preset dose"). If the dose is larger or equal to the threshold, the detector may be designated as a target detector. Merely for illustration purposes, when the dose sensors of the DR system 100 detect radiation rays emitted from the X-ray source, the determination module 530 may monitor (e.g., by determining the doses of the radiation rays) radiation doses detected by the dose sensors in real time. The determination module 530 may determine whether a dose of radiation rays (e.g., the X-rays) obtained by each of the dose sensors is larger or equal to the preset dose. If a dose of radiation rays (e.g., X-rays) detected by a dose sensor is larger than or equal to a preset dose, the direction module 520 may direct an imaging detector corresponding to the dose sensor to obtain radiation rays (e.g., the X-rays) emitted from the radiation source. If doses of radiation rays detected by at least two dose sensors are larger than or equal to the preset dose, the direction module 520 may direct at least two imaging detectors corresponding to the at least two dose sensors to obtain radiation rays (e.g., the X-rays) emitted from the radiation source.

In some embodiments, if doses of radiation rays detected by at least two dose sensors are larger than or equal to the preset dose, the direction module 520 may direct an imaging detector corresponding to one of the at least two dose sensors to obtain radiation rays (e.g., the X-rays) emitted from the radiation source. The dose detected by the one of the at least two dose sensors may be the largest dose of the radiation rays (e.g., X-rays) among the doses detected by the at least two dose sensors.

The direction module 520 may further direct the dose sensors to stop detecting radiation rays immediately after the direction module 520 directs the imaging detector(s) to obtain radiation rays emitted from the radiation source for generating an image, such that the DR system 100 may not generate a plurality of images based on radiation rays obtained by the multiple detectors of the DR system 100, which may increase the complexity of subsequent image processing. In some embodiment, the preset threshold may be determined based on actual requirements for imaging. For example, different tissues may have different preset thresholds. In some embodiments, the preset threshold may be determined according to empirical data.

In a conventional DR system, a detector matches an imaging mode (e.g., a standing position mode, a lying position mode, etc.) in the imaging process. For example, in the DR system a detector 1 may be installed in a chest film magazine in a standing position imaging mode, and a detector 2 may be installed in a flat-bed film magazine in a lying position imaging mode. The detector 1 is different from the detector 2. An incorrect installation of a detector may result in no image of the target object to be generated. For example, when the target object is in a lying position, the DR system may not generate an image of the target object using the detector 1 installed in the chest film magazine, and the target object may be exposed to unnecessary X-ray radiation. In order to avoid this problem, the conventional DR system needs to identify the detector used in the imaging process and an installation position of the detector by physically labeling the detector, then match this detector and its location with an imaging mode. For example, if the DR system identifies that the detector 1 is installed in the flat-bed film magazine, the DR system may match the detector with the lying position imaging mode. In some embodiments, the film magazine in which a detector is installed may be updated so as to determine whether a detector installed in the film magazine is matched to a corresponding imaging mode. Traditional technology may need improvement on hardware structure of the detector and/or the film magazine in which a detector is installed. The imaging process in the present disclosure may identify the detector without the help of hardware components (e.g., physical labels), which may reduce manufacturing costs of the DR system. Therefore, the reliability of the DR system may be improved without updating its hardwares. Moreover, in the conventional DR system, a particular detector may need to match a particular imaging mode, which increases complexity of the imaging process. With the system/method described in the present disclosure, a detector may not need to be exclusively used in a particular imaging mode, which may reduce the complexity of the DR system. A detector may be used in a plurality of imaging modes, thus improving extensibility of the DR system to some extent.

It should be noted that the above description of the process 600 is merely provided for the purposes of illustration, and not intended to limit the scope of the present disclosure. For persons having ordinary skills in the art, multiple variations and modifications may be made under the teachings of the present disclosure. In some embodiments, one or more operations in the process 600 may be omitted and/or one or more additional operations may be added to the process 600. For example, an operation for generating and/or outputting the image of the target object may be added after operation 630. In some embodiments, the DR system 100 may direct a portion of the multiple dose sensors to detect doses of radiation rays emitted from a radiation source of the imaging device 110. For example, the DR system 100 may direct one or more dose sensors that are located in the radiation range of the X-ray source to detect doses of radiation rays emitted from a radiation source of the imaging device 110. However, those variations and modifications do not depart from the scope of the present disclosure.

Figure 7:
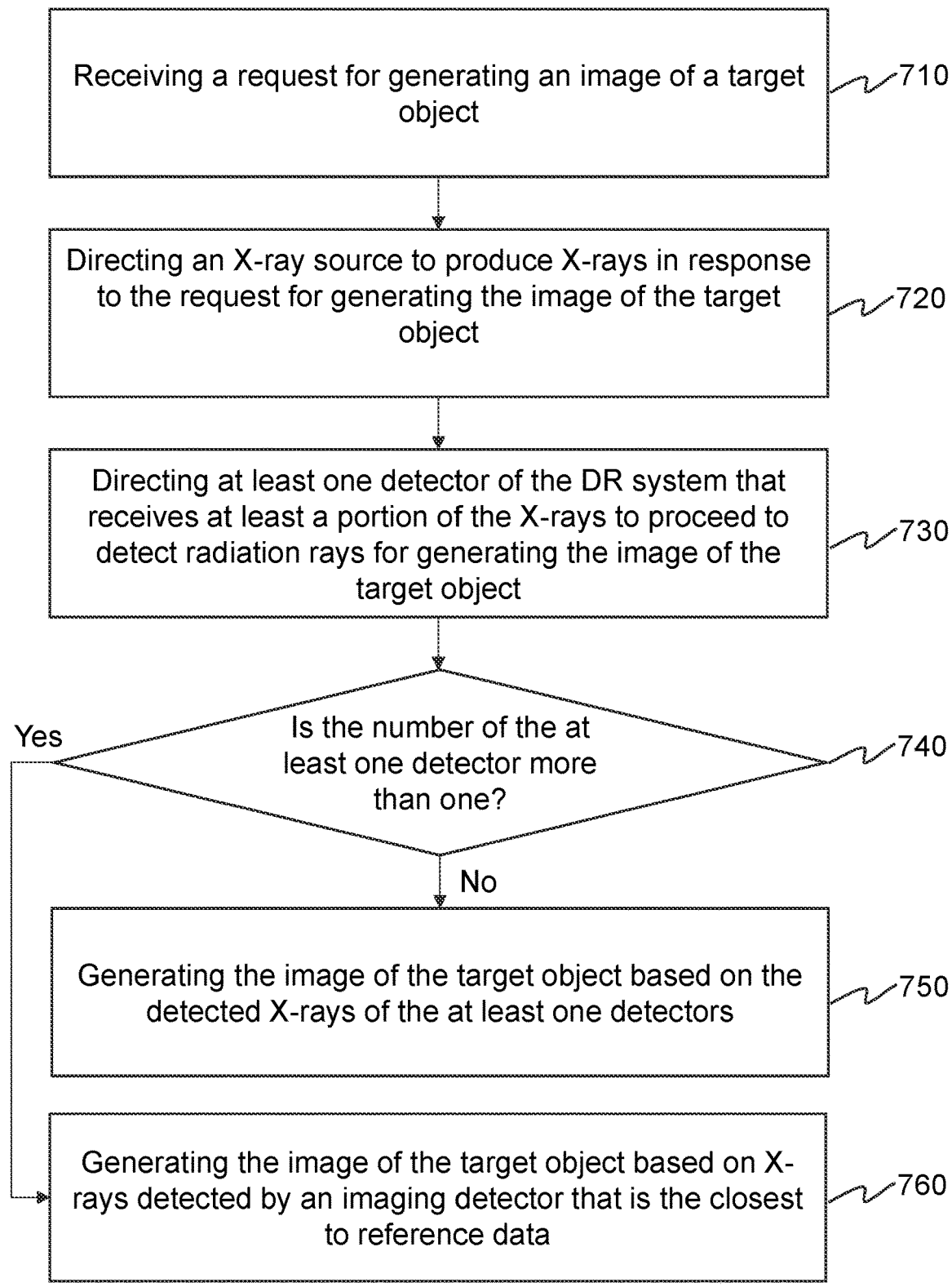
FIG. 7 is a flowchart illustrating an exemplary process for generating an image of a target object according to some embodiments of the present disclosure.

FIG. 7 is a flowchart illustrating an exemplary process for generating an image of a target object according to some embodiments of the present disclosure. In some embodiments, one or more operations of process 700 illustrated in FIG. 7 for imaging may be implemented in the DR system 100 illustrated in FIG. 1. For example, the process 700 illustrated in FIG. 7 may be stored in the storage device 130 in the form of instructions, and invoked and/or executed by the processing device 120 (e.g., the processor 210 of the computing device 200 as illustrated in FIG. 2, the CPU 340 of the mobile device 300 as illustrated in FIG. 3). As another example, a portion of the process 700 may be implemented on the X-ray imaging device 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 7 and described below is not intended to be limiting.

In 710, the processing device 120 (e.g., the obtaining module 510) may receive a request for generating an image of a target object. The request may be sent by a user or the DR system 100 automatically. For example, the user and/or the DR system 100 may send the request after the gantry 112 of the DR system 100 is moved to a designated position. In some embodiments, operations in 710 may be the same as or similar to the operations in 610.

In 720, the processing device 120 (e.g., the direction module 520) may direct an X-ray source to produce X-rays in response to the request for generating the image of the target object. The direction module 520 may direct the X-ray source to generate or emit X-rays after the obtaining module 510 receives the request. In some embodiments, operations in 720 may be the same as or similar to the operations in 620.

In 730, the processing device 120 (e.g., the direction module 520) may direct at least one detector of the DR system 100 that receives at least a portion of the X-rays to proceed to detect radiation rays for generating the image of the target object. In some embodiments, the DR system 100 may include multiple detectors. Each of the multiple detectors may include a dose sensor and an imaging detector, i.e. multiple dose sensors include in the multiple detectors correspond to multiple imaging detectors include in the multiple detectors, respectively. The direction module 520 may direct multiple dose sensors of the multiple detectors to detect doses of radiation rays emitted from the radiation source of the imaging device 110. Then the determination module 530 may determine the doses of the radiation rays detected by the multiple dose sensors. Then the direction module 520 may direct, based on doses of radiation rays (e.g., X-rays) detected by the multiple dose sensors of the DR system 100, at least one imaging detector of multiple imaging detectors corresponding to the multiple dose sensors to proceed to detect the radiation rays for generating an image of a target object to be examined. In some embodiments, operations in 730 may be the same as or similar to the operations in 630.

In 740, the processing device 120 (e.g., the determination module 530) may determine whether the number of the at least one detector is more than one. In some embodiments, the determination module 530 may determine whether the number of the imaging detectors needed to detect the radiation rays is more than one. If the number of the imaging detectors needed to detect the radiation rays is one (i.e., there is only one imaging detector needed to detect radiation rays emitted from the radiation source), the process 700 may proceed to 750. If the number of the imaging detectors needed to detect the radiation rays is larger than one (i.e., there is more than one imaging detector needed to obtain radiation rays (e.g., X-rays) emitted from the radiation source), the process 700 may proceed to 760.

In 750, the processing device 120 (e.g., the generation module 540) may generate the image of the target object based on the detected radiation rays (e.g., X-rays) of the at least one detector. In some embodiments, the generation module 540 may obtain a signal from the only one imaging detector needed to detect radiation rays after the direction module 520 directs the imaging detector to proceed to detect the radiation rays for generating the image of a target object to be examined. The obtained signal may be a digital signal including information of the detected radiation rays (e.g., attenuation information of X-rays). The generation module 540 may generate an image based on the obtained signal. Since there is only one detector (or only one imaging detector) which is used to obtain radiation rays for imaging, the generation module 540 may generate only one image in one imaging process. The determination module 530 may designate the only one image as the image of the target object.

In 760, the processing device 120 (e.g., the generation module 540) may generate the image of the target object based on radiation rays (e.g., X-rays) detected by an imaging detector that is the closest to reference data. In some embodiments, the obtaining module 510 may store the detected radiation rays in forms of radiation data. The obtaining module 510 may obtain radiation data from the more than one of the at least one imaging detector. The reference data may include data containing reference feature information of a region of interest to be examined. In some embodiments, the reference feature information may be determined by obtaining grayscale values of historical images or template images of an organ/tissue or anatomical features of an organ/tissue. For example, if the anatomical features of an organ/tissue are used as the reference feature information, an entire anatomical image of the organ/tissue may be designated as the reference feature information. In some embodiments, the reference feature information may be determined based on structure features represented by a plurality of feature points. The feature points may be selected from the anatomical structure of the organ/tissue (e.g., a marginal bone tissue). The reference data may be pre-stored in the DR system 100 (e.g., the storage device 130), or stored in an independent database (e.g., an external database of the DR system 100) for being retrieved if necessary. In some embodiments, the generation module 540 may generate the image of the target object based on the radiation data that is the closest to the reference data.

In some embodiments, the generation module 540 may generate, based on the detected radiation rays, more than one image corresponding to the more than one detector. The determination module 530 may compare each of the more than one image with the reference data (e.g., the entire anatomical image of the organ/tissue) to obtain a similarity value. The determination module 530 may designate an image that has the highest similarity value as the image of the target object. Details regarding the generation of the image of the target object may be found elsewhere in the present disclosure, for example, in FIG. 8 and the descriptions thereof.

It should be noted that the above description of the process 700 is merely provided for the purposes of illustration, and not intended to limit the scope of the present disclosure. For persons having ordinary skills in the art, multiple variations and modifications may be made under the teachings of the present disclosure. In some embodiments, one or more operations in the process 700 may be omitted and/or one or more additional operations may be added to the process 700. For example, an operation may be added after operation 760 and/or 750 to output and/or further post-process the image of the target object. However, those variations and modifications do not depart from the scope of the present disclosure.

Figure 8:
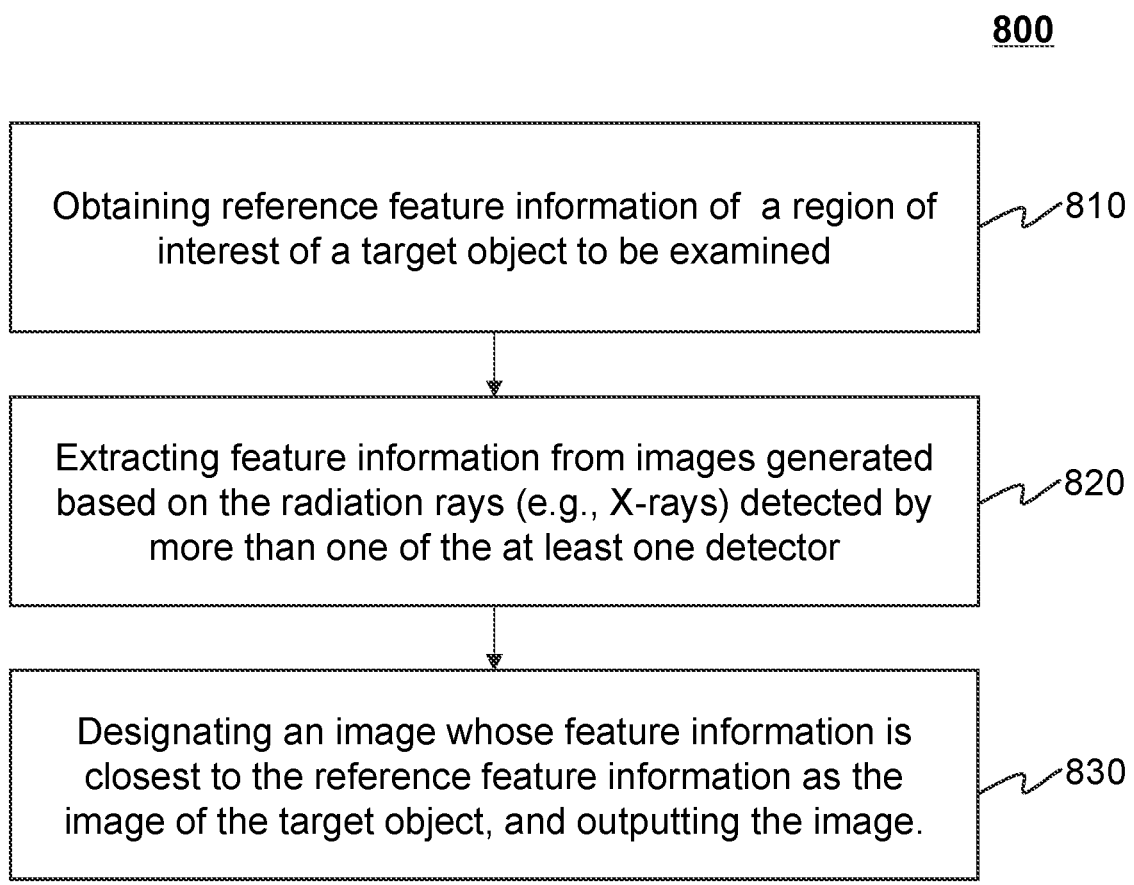
FIG. 8 is a flowchart illustrating an exemplary process for generating an image of a target object based on reference data according to some embodiments of the present disclosure.

FIG. 8 is a flowchart illustrating an exemplary process for generating an image of a target object based on reference data according to some embodiments of the present disclosure. In some embodiments, one or more operations of process 800 illustrated in FIG. 8 for imaging may be implemented in the DR system 100 illustrated in FIG. 1. For example, the process 800 illustrated in FIG. 8 may be stored in the storage device 130 in the form of instructions, and invoked and/or executed by the processing device 120 (e.g., the processor 210 of the computing device 200 as illustrated in FIG. 2, the CPU 340 of the mobile device 300 as illustrated in FIG. 3). As another example, a portion of the process 800 may be implemented on the X-ray imaging device 110. In some embodiments, operations in 760 as illustrated in FIG. 7 may be performed according to the process 800. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 8 and described below is not intended to be limiting.

In 810, the processing device 120 (e.g., the determination module 530) may obtain reference feature information of a region of interest of a target object to be examined. The reference feature information may refer to feature information extracted from a historical image of the target object or a template image including the region of interest. The historical image of the target object may be generated by scanning the target object when the target object is in a normal state (e.g., a healthy state for a person). The reference feature information may be determined by obtaining grayscale values of historical images or template images of an organ/tissue or anatomical features of an organ/tissue. The reference feature information may be pre-stored in the DR system 100 (e.g., the storage device 130), or stored in an independent database (e.g., an external database of the DR system 100) for being retrieved if necessary.

In some embodiments, the request for generating an image of the target object may include information of the region of interest to be examined of the target object. The determination module 530 may obtain the information of the region of interest from the request, and proceed to obtain the reference feature information corresponding to the region of interest.

In 820, the processing device 120 (e.g., the determination module 530) may extract feature information from images generated based on the radiation rays (e.g., X-rays) detected by more than one of the at least one detector. In some embodiments, the determination module 530 may extract the feature information by determining gray values and/or anatomical features of an organ/tissue in each of the more than one image generated based on the detected radiation rays. For example, the determination module 530 may extract feature information by determining gray values of each the more than one image generated based on the detected radiation rays.

In 830, the processing device 120 (e.g., the determination module 530) may designate an image whose feature information is closest to the reference feature information as the image of the target object, and output the image.

In some embodiments, the determination module 530 may compare the extracted feature information of each image with the reference feature information to obtain a similarity value. The determination module 530 may determine feature information of an image that has the highest similarity value by comparing feature information of each image with the reference feature information. The determination module 530 may designated an image whose feature information possesses the highest similarity value as the image of the target object.

In some embodiments, the determination module 530 may simply compare extracted feature information of each image with the reference feature information by determining differences between the extracted feature information of each image and the reference feature information. In some embodiments, the determination module 530 may compare extracted feature information of each image with the reference feature information using a particular algorithm for determining correlations between the extracted feature information and the reference feature information. The finally determined image of the target object, based on comparison among a plurality of obtained images, may better satisfy actual requirements of clinical diagnosis.

In some embodiments, the determined image above may be an initial image of the target object. The initial image may be further processed by multiple optimization, for example but not limited to denoising, filtering, enhancing, or gray-level transformation, etc., to obtain a processed image of the target object. The processed image may have a higher contrast, which may show details of the initial image clearer and have a better display effect of the initial image.

It should be noted that the above description of the process 800 is merely provided for the purposes of illustration, and not intended to limit the scope of the present disclosure. For persons having ordinary skills in the art, multiple variations and modifications may be made under the teachings of the present disclosure. In some embodiments, one or more operations in the process 800 may be omitted and/or one or more additional operations may be added to the process 800. For example, operation 830 may be separated into two operations. One of the two operations may be for comparing the feature information and the reference feature information, another one of the two operations may be for designating an image as the image of the target object. Thus, the finally determined image of the target object may satisfy actual requirements of clinical diagnosis. However, those variations and modifications do not depart from the scope of the present disclosure.

Figure 9:
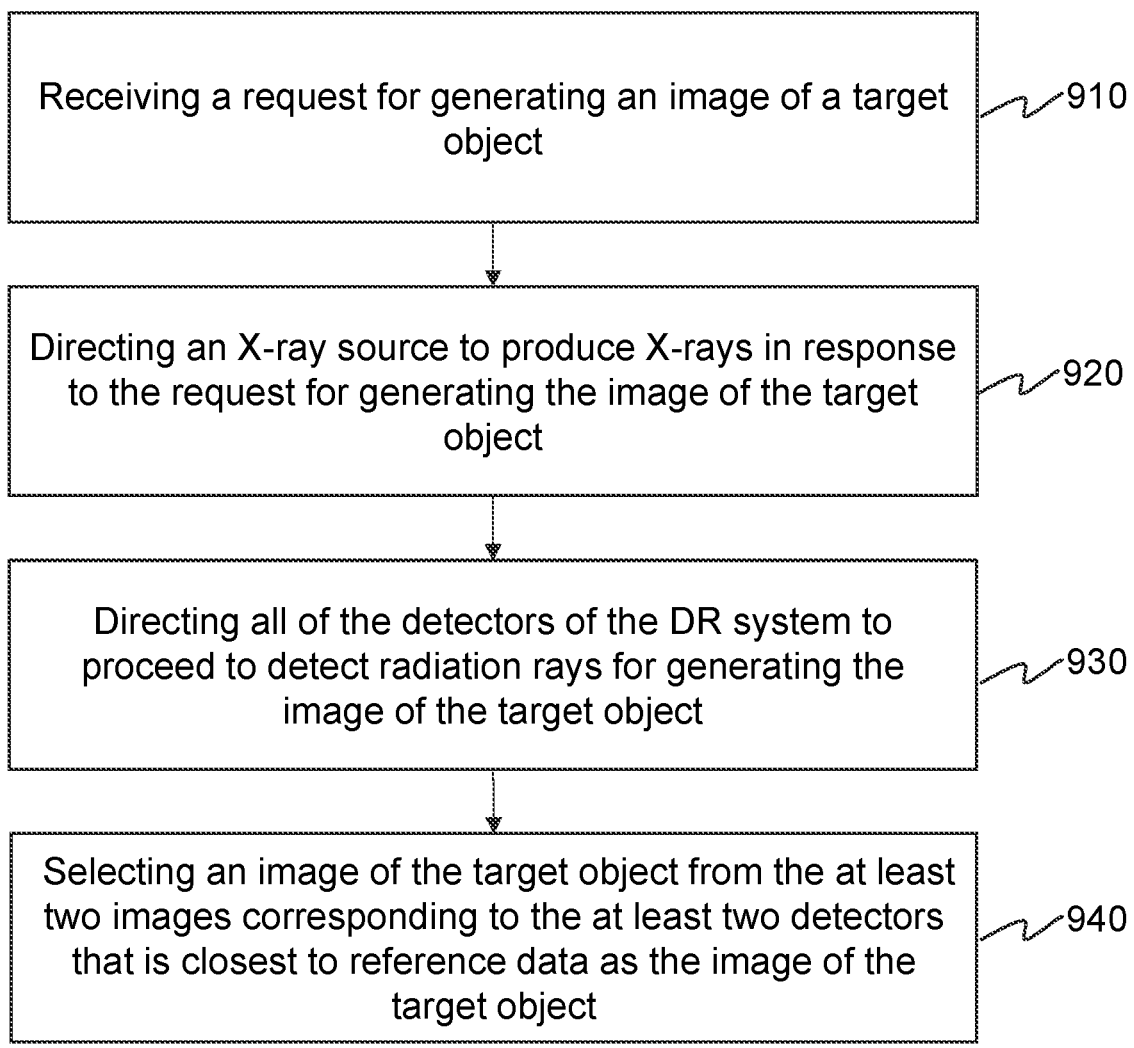
FIG. 9 is a flowchart illustrating an exemplary process for generating an image of a target object according to some embodiments of the present disclosure.

FIG. 9 is a flowchart illustrating an exemplary process for generating an image of a target object according to some embodiments of the present disclosure. In some embodiments, one or more operations of process 900 illustrated in FIG. 9 for imaging may be implemented in the DR system 100 illustrated in FIG. 1. For example, the process 900 illustrated in FIG. 9 may be stored in the storage device 130 in the form of instructions, and invoked and/or executed by the processing device 120 (e.g., the processor 210 of the computing device 200 as illustrated in FIG. 2, the CPU 340 of the mobile device 300 as illustrated in FIG. 3). As another example, a portion of the process 900 may be implemented on the X-ray imaging device 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 9 and described below is not intended to be limiting.

In 910, the processing device 120 (e.g., the obtaining module 510) may receive a request for generating an image of a target object. The request may be sent by a user or the DR system 100 automatically. For example, the user and/or the DR system 100 may send the request after the gantry 112 of the DR system 100 is moved to a designated position. In some embodiments, operations in 910 may be the same as or similar to the operations in 610.

In 920, the processing device 120 (e.g., the direction module 520) may direct an X-ray source to produce X-rays in response to the request for generating the image of the target object. The direction module 520 may direct the X-ray source to generate or emit X-rays after the obtaining module 510 receives the request. In some embodiments, operations in 920 may be the same as or similar to the operations in 620.

In 930, the processing device 120 (e.g., the direction module 520) may direct all of the detectors of the DR system 100 to proceed to detect radiation rays (e.g., X-rays) for generating the image of the target object. In some embodiments, the DR system 100 may include at least two detectors. The at least two detectors may detect radiation rays emitted from the radiation source, and generate at least two images corresponding to the at least two detectors. In some embodiments, the detectors used in the process 900 may be different from the detectors used in the process 600 through 800. Each of the detectors used in the process 900 may be or only include an imaging detector. The processing device 120 may not need to direct the detectors to proceed to detect the radiation rays for generating an image of a target object to be examined based on radiation doses obtained by dose sensors corresponding to the imaging detectors in comparison with operations in 630.

In 940, the processing device 120 (e.g., the determination module 530) may select an image of the target object from the at least two images corresponding to the at least two detectors that is closest to reference data as the image of the target object. Details of the reference data may be found elsewhere in the present disclosure, for example, in 760 of FIGS. 7 and 830 of FIG. 8 and the descriptions thereof. The determination module 530 may obtain reference data associated with a region of interest of the target object to be examined. The determination module 530 may extract feature information from images generated based on the radiation rays detected by all of the detectors. The determination module 530 may designate an image whose feature information is closest to the reference data as the image of the target object. In some embodiments, operations in 940 may be the similar with process 800.

The above method may enable all of detectors of the DR system 100 to detect radiation rays for imaging simultaneously, so that an output image (e.g., an image of the target object) may be determined based on similarity values between images generated based on radiation data from all of the detectors and the reference data, thereby ensuring that the output image may meet actual clinical requirements. The image generation method above may be realized without using other hardware components to identify a particular detector, which helps to reduce manufacturing costs.

The above method may be further described in combination with a specific application scenario in which a patient is taken as an example. The patient may register, for example, on a medical platform, information including identity information of the patient, and a region of interest to be examined before he/she is examined using the DR system 100. An information card including the registered information may be provided to the patient. When the patient enters an examination room taking the information card, the DR system 100 and/or a user (e.g., a technician or a doctor) may read and recognize information such as the identity information of the patient and/or the region of interest to be examined in the information card. The DR system 100 and/or the user may direct the gantry 112 of DR system 100 and/or the patient to move to designated positions based on the information obtained from the information card. After the gantry 112 and/or the patient is moved to the designated positions, the DR system 100 and/or the user (e.g., the user pressing an exposure hand brake) may direct the X-ray source of the DR system 100 to produce X-rays. All of the detectors may be directed to receive radiation rays (e.g., X-rays) and generate images based on the received radiation rays (without determining doses of the radiation rays). Images generated based on radiation rays obtained by all the detectors may be sent to the processing device 120 (e.g., the controller 410). In some embodiments, the processing device 120 may determine an image from the generated images that meets actual clinical requirements according to feature information such as gray scale information of the images, and then output the image for clinical diagnosis.

It should be noted that the above description of the process 900 is merely provided for the purposes of illustration, and not intended to limit the scope of the present disclosure. For persons having ordinary skills in the art, multiple variations and modifications may be made under the teachings of the present disclosure. For example, the process 900 may be applied to an imaging system without dose sensors. As another example, the process 900 may be applied to an imaging system with dose sensors. However, those variations and modifications do not depart from the scope of the present disclosure.

Figure 10:
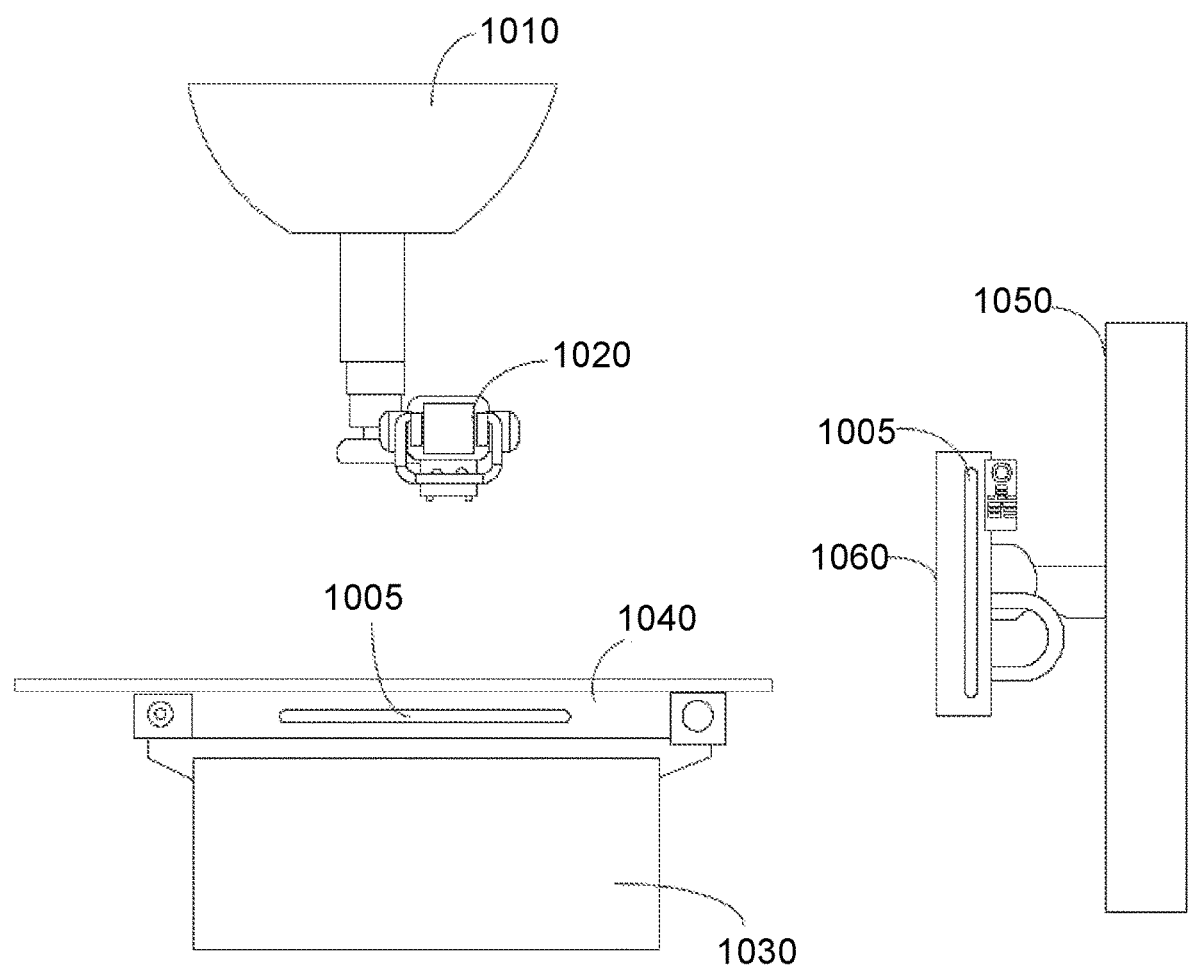
FIG. 10 is schematic diagram illustrating an exemplary DR system according to some embodiments of the present disclosure.

FIG. 10 is schematic diagram illustrating an exemplary DR system according to some embodiments of the present disclosure. As illustrated in FIG. 10, the DR system 1000 may include a gantry 1010, an X-ray source 1020, two radiation detectors 1005, a flat-bed 1030, a first film magazine 1040 (also referred to as a flat-bed film magazine), a column 1050, a second film magazine 1060 (also referred to as a chest film magazine), and a controller (not shown). The first film magazine 1040 may be installed on the flat-bed 1030. The second film magazine 1060 may be installed on the column 1050. The first film magazine 1040 and the second film magazine 1060 may be configured to accommodate the detectors 1005.

In some embodiments, the X-ray source 1020 may be disposed opposite to the two radiation detectors 1005, for example, installing on the gantry 1010. The X-ray source 1020's relative position between the two radiation detectors 1005 may be adjustable, for example, moving with the gantry 1010 to a proper position.

In some embodiments, a detector 1005 may have a flat plate shape, and may also be referred to as a flat panel detector. The two detectors 1005 may be located in a first orientation (e.g., a first geometric surface) and a second orientation (e.g., a second geometric surface), respectively. The first orientation and the second orientation may form an angle between 60 degrees and 120 degrees. The angle may be preset according to clinical requirements. For example, when the angle is set to be 90 degrees, the first orientation may be perpendicular to the second orientation, i.e., the two detectors 1005 may be perpendicular to each other (or the first film magazine 1040 may be perpendicular to the second film magazine 1060 (as shown in FIG. 10).

In some embodiments, the two detectors 1005 may have the same structure (e.g., a wireless flat panel structure), such that there is no need to set labels for identifying the two detectors 1005. The two detectors 1005 may be installed in any one of the first film magazine 1040 or the second film magazine 1060 to operate normally. The DR system 100 described in the present disclosure may help to avoid, due to the misplacement of the detectors, no image resulted but that a target object receives unnecessary radiation in an imaging process, and thereby, enhancing reliability of the DR system 100.

In some embodiments, the controller (not shown) may be configured to receive an image acquisition instruction. The image acquisition instruction may include a request for generating an image of a target object to be examined. In some embodiments, the controller may control the X-ray source 1020 based on the image acquisition instruction. For example, the controller may direct the X-ray source 1020 to produce (or provide) X-rays according to the image acquisition instruction. In some embodiments, the controller may control the two radiation detectors 1005 to detect radiation rays. For example, the controller may initiate one of the two radiation detectors 1005 to acquire radiation rays (e.g., X-rays) based on at least a portion of the X-rays received by the two radiation detectors 1005. The controller may then generate the image of the target object based on the radiation rays acquired by the one of the two radiation detectors. More specifically, each of the two radiation detectors 1005 may include a dose sensor and an imaging detector. The controller may first initiate the dose sensors of the two radiation detectors 1005 to receive at least a portion of X-rays, and determine doses of the portion of X-rays received by the two radiation detectors 1005. The controller may direct an imaging detector corresponding to a dose sensor of which the detected dose is higher to receive radiation rays (e.g., X-rays) for generating the image of the target object, and stop the dose sensors simultaneously. As another example, the controller may initiate the two radiation detectors 1005 to acquire radiation rays (e.g., X-rays). The controller may generate the image of the target object based on the radiation rays (e.g., X-rays) acquired by the two radiation detectors 1005. More specifically, the controller may compare images generated based on the acquired radiation rays with reference data associated with the target object to determine the image of the target object.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a medical imaging system, the medical imaging system including a radiation source, multiple imaging detectors, and a computing device, the computing device including at least one processor and at least one storage device, the method comprising:
    obtaining a request for generating an image of a target object;
    directing the radiation source to produce radiation rays in response to the request; and
    directing, based on at least a portion of the radiation rays received by the multiple imaging detectors, at least one of the multiple imaging detectors to proceed to detect the radiation rays for generating the image of the target object.

2. The method of claim 1, further comprising:
    determining whether a count of the at least one of the multiple imaging detectors is more than one.

3. The method of claim 2, further comprising:
    in response to a determination that the count of the at least one of the multiple imaging detectors is one, designating an image generated by the one imaging detector as the image of the target object.

4. The method of claim 2, further comprising:
    in response to a determination that the number of the at least one of the multiple imaging detectors is more than one, designating an image generated by one of the more than one imaging detectors as the image of the target object.

5. The method of claim 4, wherein the designating an image generated by one of the at least one of the multiple imaging detectors as the image of the target object includes:
    obtaining reference feature information of the region of interest of the target object;
    extracting feature information from images generated by the more than one imaging detectors; and
    designating an image whose feature information is closest to the reference feature information as the image of the target object.

6. The method of claim 5, wherein the reference feature information includes feature information extracted from a historical image of the target object or a template image including the region of interest.

7. The method of claim 6, wherein the historical image of the target object is generated by scanning the target object when the target object is in a normal state.

8. The method of claim 1, wherein the directing, based on at least a portion of the radiation rays received by the multiple imaging detectors, at least one of the multiple imaging detectors to proceed to detect the radiation rays for generating the image of the target object includes:
    determining doses of the portion of the radiation rays received by the multiple imaging detectors; and directing, based on the doses, the at least one of the multiple imaging detectors to proceed to detect the radiation rays for generating the image of the target object.

9. The method of claim 8, wherein a dose of the portion of the radiation rays received by the at least one of the multiple imaging detectors is larger than or equal to a preset dose.

10. The method of claim 1, wherein the medical imaging system includes a digital radiography system.

11. A medical imaging system including a radiation source and multiple imaging detectors, the system comprising:
at least one storage device storing a set of instructions; and
at least one processor in communication with the at least one storage medium, wherein when executing the set of instructions, the at least one processor is configured to cause the system to perform operations including:
obtaining a request for generating an image of a target object;
directing the radiation source to produce radiation rays in response to the request; and
directing, based on at least a portion of the radiation rays received by the multiple imaging detectors, at least one of the multiple imaging detectors to proceed to detect the radiation rays for generating the image of the target object.

12. The system of claim 11, wherein the operations further include:
determining whether a count of the at least one of the multiple imaging detectors is more than one.

13. The system of claim 12, wherein the operations further include:
in response to a determination that the count of the at least one of the multiple imaging detectors is one, designating an image generated by the one imaging detector as the image of the target object.

14. The system of claim 12, wherein the operations further include:
in response to a determination that the count of the at least one of the multiple imaging detectors is more than one, designating an image generated by one of the more than one imaging detectors as the image of the target object.

15. The system of claim 14, wherein the designating an image generated by one of the at least one of the multiple imaging detectors as the image of the target object includes:
obtaining reference feature information of the region of interest of the target object;
extracting feature information from images generated by the more than one imaging detectors; and
designating an image whose feature information is closest to the reference feature information as the image of the target object.

16. The system of claim 15, wherein the reference feature information includes feature information extracted from a historical image of the target object or a template image including the region of interest.

17. The system of claim 16, wherein the historical image of the target object is generated by scanning the target object when the target object is in a normal state.

18. The system of claim 11, wherein the directing, based on at least a portion of the radiation rays received by the multiple imaging detectors, at least one of the multiple imaging detectors to proceed to detect the radiation rays for generating the image of the target object includes:
determining doses of the portion of the radiation rays received by the multiple imaging detectors; and
directing, based on the doses, the at least one of the multiple imaging detectors to proceed to detect the radiation rays for generating the image of the target object.

19. The system of claim 18, wherein a dose of the portion of the radiation rays received by the at least one of the multiple imaging detectors is larger than or equal to a preset dose.

20. A non-transitory computer readable medium, comprising at least one set of instructions, wherein when executed by at least one processor of a computing device, the at least one set of instructions cause the at least one processor to effectuate a method implemented on a medical imaging system, the medical imaging system including a radiation source and multiple imaging detectors, comprising:
obtaining a request for generating an image of a target object;
directing the radiation source to produce radiation rays in response to the request; and
directing, based on at least a portion of the radiation rays received by the multiple imaging detectors, at least one of the multiple imaging detectors to proceed to detect the radiation rays for generating the image of the target object.

* * * * *